United States Patent
Iizuka et al.

(10) Patent No.: US 10,209,199 B2
(45) Date of Patent: Feb. 19, 2019

(54) SURFACE INSPECTION METHOD, SURFACE INSPECTION DEVICE, MANUFACTURING SYSTEM, METHOD OF IDENTIFYING DEFECT FORMED AREA, AND MANUFACTURING METHOD OF STEEL PIPE

(71) Applicant: JFE Steel Corporation, Tokyo (JP)

(72) Inventors: Yukinori Iizuka, Tokyo (JP); Hiroaki Ono, Tokyo (JP); Toshifumi Kodama, Tokyo (JP); Akihiro Ogawa, Tokyo (JP)

(73) Assignee: JFE Steel Corporation (JP)

( * ) Notice: Subject to any disclaimer, the term of this patent is extended or adjusted under 35 U.S.C. 154(b) by 173 days.

(21) Appl. No.: 15/124,807

(22) PCT Filed: Mar. 3, 2015

(86) PCT No.: PCT/JP2015/056246
§ 371 (c)(1),
(2) Date: Sep. 9, 2016

(87) PCT Pub. No.: WO2015/137200
PCT Pub. Date: Sep. 17, 2015

(65) Prior Publication Data
US 2017/0023489 A1    Jan. 26, 2017

(30) Foreign Application Priority Data

Mar. 12, 2014   (JP) .................................. 2014-049163

(51) Int. Cl.
*G01N 21/88* (2006.01)
*G01J 5/00* (2006.01)
(Continued)

(52) U.S. Cl.
CPC ............ *G01N 21/8806* (2013.01); *G01J 5/48* (2013.01); *G01N 21/359* (2013.01); *G01N 21/93* (2013.01);
(Continued)

(58) Field of Classification Search
CPC .................................................... G01N 21/8806
See application file for complete search history.

(56) References Cited

U.S. PATENT DOCUMENTS 4,872,762 A * 10/1989 Koshihara .............. G01N 25/72
                                                      250/330
4,983,836 A *  1/1991 Matoba ................. G01N 25/72
                                                      250/330
(Continued)

FOREIGN PATENT DOCUMENTS

CN          1603265        4/2005
CN        101622082        1/2010
(Continued)

OTHER PUBLICATIONS

K. Iwai et al., "On-line Inspection Techniques for Surface Detects of Hot Slabs", *Iron and Steel*, 70 (9), 1984, pp. 1181-1187, with an English summary.
(Continued)

*Primary Examiner* — David P Porta
*Assistant Examiner* — Jeremy S Valentiner
(74) *Attorney, Agent, or Firm* — DLA Piper LLP (US)

(57) ABSTRACT

A surface inspection method for a steel pipe detects a surface defect on a hot steel pipe, and includes: an imaging step of imaging a self-luminous image of the hot steel pipe; a correcting step of making more uniform luminance variation in a circumferential direction of the self-luminous image and correcting the self-luminous image; and a detecting step of
(Continued)

RAW IMAGE    DISTRIBUTION IN      UNIFORMED
             CIRCUMFERENTIAL      LUMINANCE
             DIRECTION detecting a surface defect based on the self-luminous image corrected at the correcting step.

10 Claims, 8 Drawing Sheets

(51) Int. Cl.
    *G01N 25/72*     (2006.01)
    *G01J 5/48*     (2006.01)
    *G01N 21/359*     (2014.01)
    *G01N 21/93*     (2006.01)
    *G01N 21/95*     (2006.01)

(52) U.S. Cl.
    CPC ............. *G01N 21/95* (2013.01); *G01N 25/72* (2013.01); *G01J 2005/0077* (2013.01)

(56) References Cited

U.S. PATENT DOCUMENTS

| | | | |
|---|---|---|---|
| 5,654,977 A * | 8/1997 | Morris .................... | G01N 25/72 374/124 |
| 2010/0095722 A1 | 4/2010 | Nishiura et al. | |
| 2010/0232678 A1 * | 9/2010 | Hasegawa ............... | B21C 37/08 382/141 |
| 2011/0268343 A1 | 11/2011 | Groos et al. | |
| 2013/0058672 A1 | 3/2013 | Takada et al. | |

FOREIGN PATENT DOCUMENTS

| | | |
|---|---|---|
| CN | 102027362 | 4/2011 |
| CN | 202083644 | 12/2011 |
| CN | 102968035 | 3/2013 |
| CN | 102980892 | 3/2013 |
| EP | 1 326 064 | 7/2003 |
| JP | 2-12045 A | 1/1990 |
| JP | 2011-642 A | 1/2011 |
| JP | 2012-13509 A | 1/2012 |

OTHER PUBLICATIONS

T. Shiraiwa et al., "Color TV System for Inspection of Hot Slabs under Slabbing", *Iron and Steel*, 64 (13), 1978, pp. 2020-2025, with an English summary.

Notification of Reasons for Refusal of corresponding Japanese Patent Application No. 2015-536697 along with a Concise Statement of Relevance of Office Action in English.

Supplementary European Search Report dated Aug. 22, 2017, of corresponding European Application No. 15761351.4.

Kim, K, et al., "Measurement of defect thickness of the wall thinning defect pipes by lock-in infrared thermography technique," *SPIE*, vol. 7522, Apr. 10, 2014.

Chinese Office Action dated May 3, 2018, of corresponding Chinese Application No. 201580012793.1, along with a Concise Statement of Relevance of Office Action in English.

\* cited by examiner

OUTER DIAMETER 76.3mm

OUTER DIAMETER 76.3mm
(ANOTHER POSITION IN LONGITUDINAL DIRECTION)

OUTER DIAMETER 101.6mm

OUTER DIAMETER 114.3mm

RAW IMAGE   DISTRIBUTION IN   UNIFORMED
            CIRCUMFERENTIAL   LUMINANCE
            DIRECTION

RAW IMAGE   ANOTHER RAW IMAGE          UNIFORMED
            CAPTURED BEFORE RAW IMAGE  LUMINANCE

SCALE PATTERN

RAW IMAGE | DISTRIBUTION IN CIRCUMFERENTIAL DIRECTION | UNIFORMED LUMINANCE

RAW IMAGE | DISTRIBUTION IN CIRCUMFERENTIAL DIRECTION | UNIFORMED LUMINANCE

SURFACE INSPECTION METHOD, SURFACE INSPECTION DEVICE, MANUFACTURING SYSTEM, METHOD OF IDENTIFYING DEFECT FORMED AREA, AND MANUFACTURING METHOD OF STEEL PIPE

TECHNICAL FIELD

This disclosure relates to a surface inspection method, a surface inspection device, a manufacturing system, a method of identifying a defect formed area, and a manufacturing method to optically detect a defect on the surface of a steel pipe.

BACKGROUND

Defects on a steel pipe used as various kinds of pipes, critical parts of machinery, line pipes, and the like reduce its strength, toughness, and fatigue properties, and defect inspections are thus performed in manufacturing a steel pipe. Non-destructive inspections such as eddy current testing, magnetic leakage flux testing, and ultrasonic testing and eye inspection are common techniques of defect inspection. However, these techniques are less applicable to high temperature materials and are thus applied for a steel pipe, which includes a seamless steel pipe manufactured by hot rolling and a butt-welded steel pipe, after cooling down the materials. In manufacturing such kinds of steel pipes, a surface defect caused by rolling is detected only after a large number of steel pipes have undergone the rolling processing, which results in manufacturing a large number of non-conforming products. A technique is thus desired that can inspect the surface when the steel pipe is hot.

As a technique of inspecting a hot surface, for example, Iwai et al., "On-line inspection techniques for surface detects of hot slabs", Iron and Steel 70 (9), pp. 1181-1187 (1984) describes techniques that use an image (a self-luminous image) formed by using self-luminescence, an image formed by using an external light source, a thermal image formed by induction heating and techniques of using laser scanning, eddy current, and the like. Shiraiwa et al., "Color TV system for inspection of hot slabs under slabbing", Iron and Steel 64 (13), pp. 2020-2025 (1978) describes a technique of inspecting the surface of a slab using a self-luminous image. The surface temperature of a slab differs depending on whether a surface defect exists thereon, and this technique detects a surface defect based on a difference in luminance between self-luminous images.

Use of a self-luminous image for surface inspection of a steel pipe, however, has the following problem. The rolling of seamless steel pipes uses a plurality of rolls disposed in the circumferential direction. The amount of heat removed by contact of each roll is different, which results in uneven temperature on the surface of the steel pipe after the rolling. Furthermore, variations in the size of a steel pipe affect the uneven temperature on the surface in removing heat by contact with the rolls. Primary scale generated in heating and secondary scale generated in rolling may attach to the surface of a steel pipe in a "spotty" manner. Such a disturbance changes the surface temperature in patterns and causes variations in the luminance of a self-luminous image. It is thus difficult to determine whether the change in the surface temperature is caused by the disturbance or by a defect on the surface.

It could therefore be helpful to provide a surface inspection method, a surface inspection device, a manufacturing system, and a method of identifying a defect formed area of a steel pipe to detect a surface defect on the steel pipe when the steel pipe is hot using a self-luminous image.

SUMMARY

We thus provide a surface inspection method for a steel pipe that detects a surface defect on a hot steel pipe, and includes: an imaging step of imaging a self-luminous image of the hot steel pipe; a correcting step of uniformizing luminance variation in a circumferential direction of the self-luminous image and correcting the self-luminous image; and a detecting step of detecting a surface defect based on the self-luminous image corrected at the correcting step.

Moreover, the self-luminous image is captured in a position behind a reducer.

Moreover, a diameter reduction rate applied by the reducer for the steel pipe is equal to or greater than 110%.

Moreover, the correcting step uniforms luminance variation in the circumferential direction of the self-luminous image by using a luminance distribution in the circumferential direction where luminance in a longitudinal direction of the steel pipe on the self-luminous image is averaged.

Moreover, the correcting step uniforms a luminance variation in the circumferential direction of the self-luminous image by using a difference in luminance between a plurality of self-luminous images captured with a position in a longitudinal direction of the steel pipe changed.

Moreover, the imaging step captures the self-luminous image by using a bandwidth of equal to or longer than 700 nm wavelength of near infrared light and equal to or shorter than 20 μm wavelength of infrared light.

We also provide a surface inspection device for a steel pipe that detects a surface defect on a hot steel pipe, and includes: an imaging unit configured to capture a self-luminous image of the hot steel pipe; a correcting unit configured to uniform luminance variation in a circumferential direction of the self-luminous image and to correct the self-luminous image; and a detecting unit configured to detect a surface defect based on the self-luminous image corrected by the correcting step.

We further provide a steel pipe manufacturing system that includes the above-described surface inspection device for a steel pipe.

We still further provide a method of identifying a defect formed area on a steel pipe that includes: inspecting the steel pipe and detecting a surface defect on the steel pipe by using the above-described surface inspection method for a steel pipe; determining that the surface defect is caused in a steel pipe manufacturing process when regularity is seen in a position where the surface defect has been detected; and determining that the surface defect is caused at a steel making stage when no regularity is seen in the position where the surface defect has been detected.

Moreover, the steel pipe manufacturing method includes: changing a manufacturing condition in a steel pipe manufacturing process and/or an operation condition at a steel making stage to prevent generation of a surface defect based on a cause of the surface defect identified by using the above-described method of identifying a defect formed area on a steel pipe.

We can thereby detect a surface defect on a steel pipe when the steel pipe is hot by using a self-luminous image.

Figure 1:
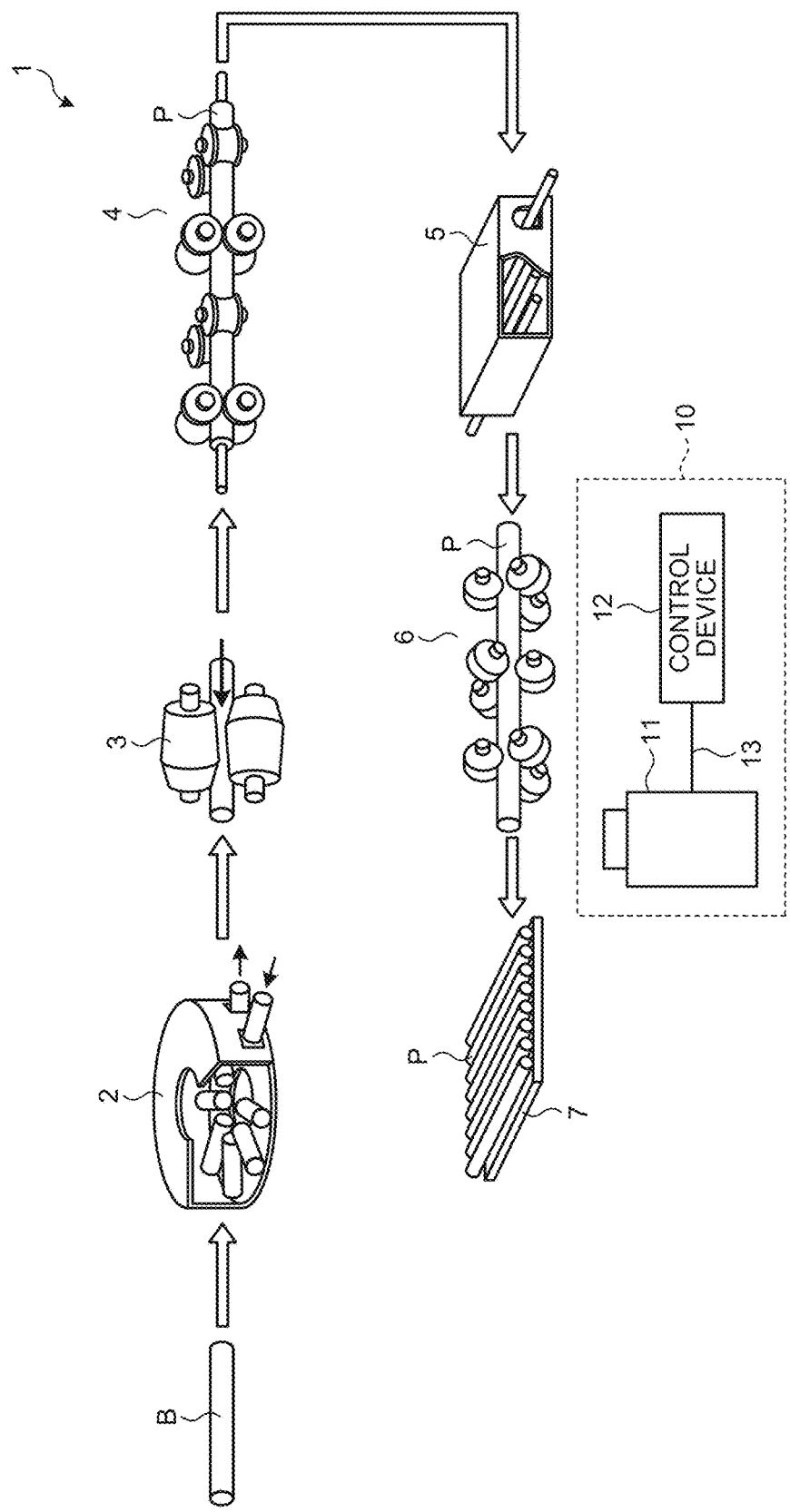
FIG. 1 is a schematic drawing that illustrates a general configuration of a manufacturing system of a seamless steel pipe according to an example.

REFERENCE SIGNS LIST 1 manufacturing system
2 furnace
3 piercer
4 mandrel mill
5 reheating furnace
6 reducer
7 cooling station
10 surface inspection device
11 thermal image camera
12 control device
13 control cable

DETAILED DESCRIPTION

An example will now be described in detail with reference to the drawings. It should be noted that this disclosure is not limited to the example and like numerals refer to like members in the drawings.

A manufacturing system of a seamless steel pipe in the example will be described with reference to FIG. 1. A manufacturing system 1 of the seamless steel pipe in the example includes a furnace 2, a piercer 3, a mandrel mill 4, a reheating furnace 5, a reducer 6, a cooling station 7, and a surface inspection device 10. With the manufacturing system 1, the furnace 2 heats a round billet (a round steel piece) B up to around 1200° C., and the piercer 3 forms a steel pipe (a seamless pipe) P from the billet. The mandrel mill 4 thereafter rolls the steel pipe. The reheating furnace 5 reheats the steel pipe P, and the reducer 6 elongates the pipe by rolling to a certain outer diameter. The cooling station 7 thereafter cools the pipe.

The surface inspection device 10 includes a thermal image camera 11 and a control device 12. The thermal image camera 11 connects to the control device 12 through a control cable 13 in a data transmittable and receivable manner. The thermal image camera 11 is configured with a camera having a complementary metal oxide semiconductor (CMOS) element, a microborometer element or the like sensitive to the bandwidth of equal to or longer than 700 nm wavelength of near infrared light and equal to or shorter than 20 μm wavelength of infrared light. The thermal image camera 11 captures a self-luminous image of the steel pipe P in a position behind the reducer 6 and transmits the self-luminous image to the control device 12.

The control device 12 is implemented by a general purpose computer such as a workstation and a personal computer. The control device 12 is configured with a central processing unit (CPU), various kinds of recording devices, which include memories such as a read only memory (ROM) including an update recordable flash memory and a random access memory (RAM), a hard disk, and a recording medium such as a compact disc read only memory (CD-ROM), a communication device, an output device such as a display device and a printing device, an input device, and others. The control device 12 controls the configuration unit of the surface inspection device 10 using a memory storing therein a processing program and others, a CPU executing the processing program and the like and executes later-described surface inspection processing.

Figure 2:
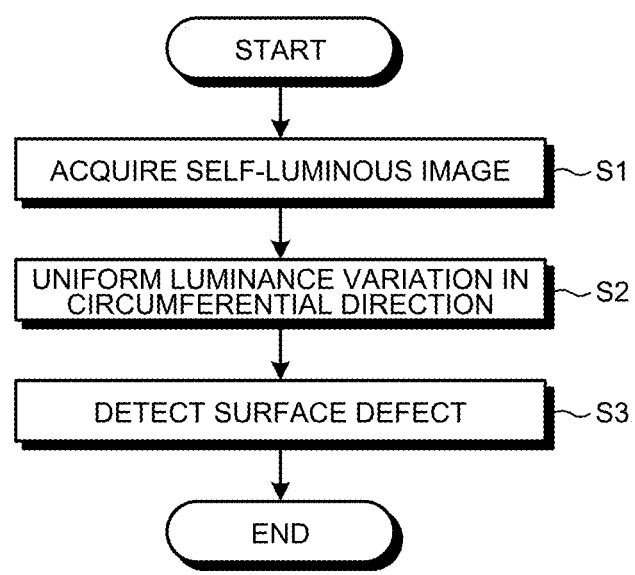
FIG. 2 is a flowchart that illustrates a procedure of surface inspection processing in the example.

The procedure of the surface inspection processing of the steel pipe P performed by the surface inspection device 10 will now be described with reference to the flowchart in FIG. 2. The flowchart in FIG. 2 starts, for example, at a timing an operator inputs an instruction for the inspection start by operating the input device of the control device 12. The surface inspection processing proceeds to the processing at Step S1.

At the processing at Step S1, the control device 12 acquires a self-luminous image of the steel pipe P captured by the thermal image camera 11 in a predetermined frequency. The processing at Step S1 is completed and the surface inspection processing proceeds to the processing at Step S2.

Figure 3A:
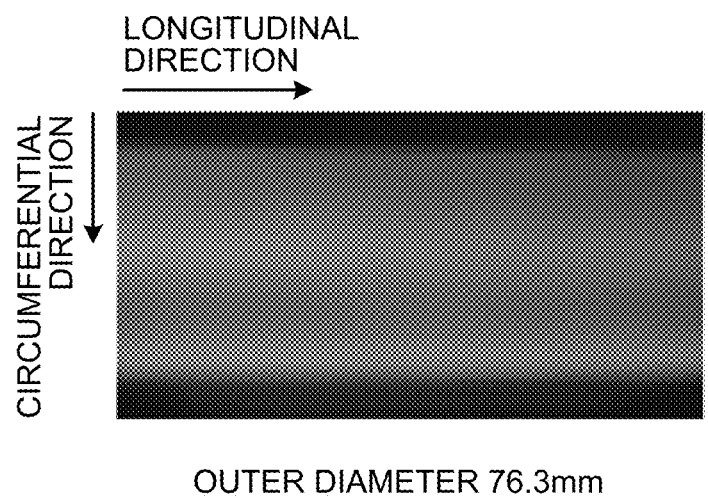
FIG. 3A is an illustrative drawing showing the relationship between the position and the size of a steel pipe on a self-luminous image in the example.
Figure 3B:
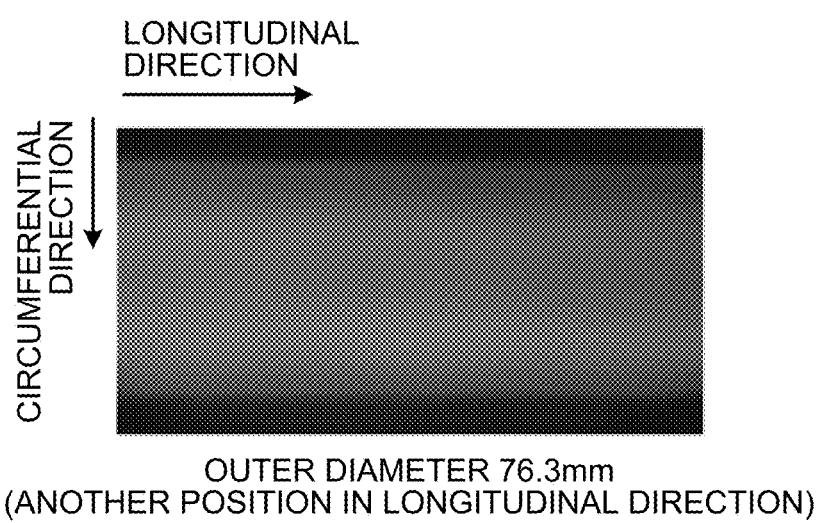
FIG. 3B is another illustrative drawing showing the relationship between the position and the size of a steel pipe on the self-luminous image in the example.
Figure 3C:
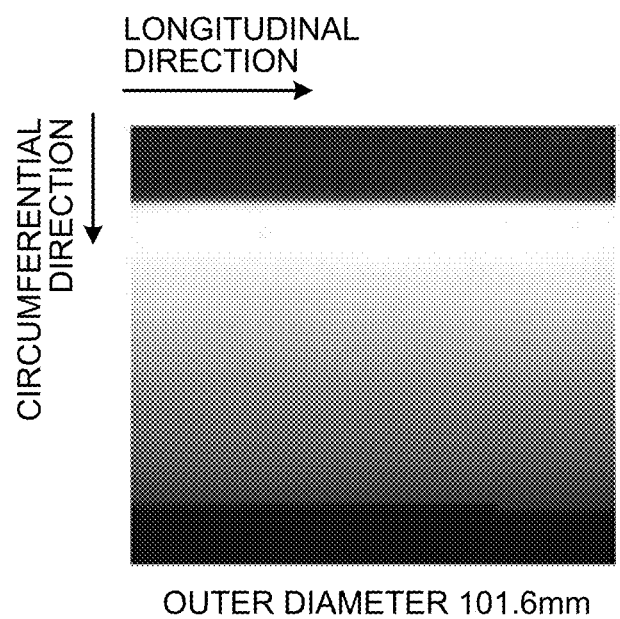
FIG. 3C is still another illustrative drawing showing the relationship between the position and the size of a steel pipe on the self-luminous image in the example.
Figure 3D:
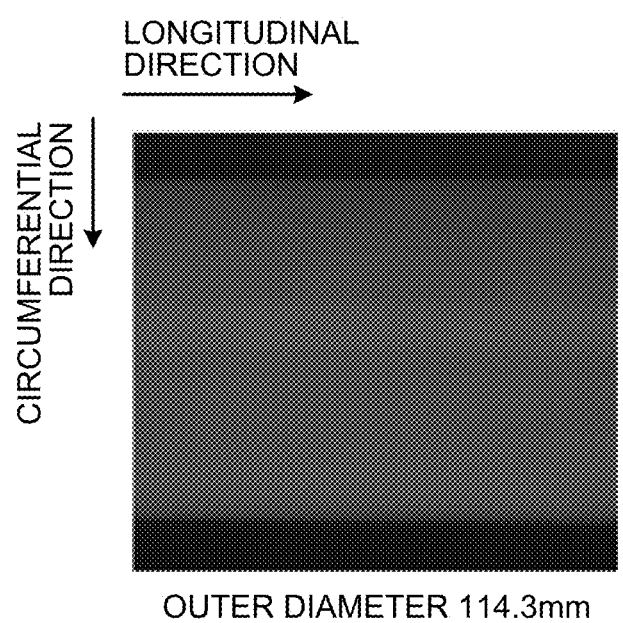
FIG. 3D is still another illustrative drawing showing the relationship between the position and the size of a steel pipe on the self-luminous image in the example.

The surface temperature, which represents the luminance of the self-luminous image, varies depending on the position and the size of the steel pipe. FIGS. 3A and 3B are self-luminous images of the steel pipe P having an outer diameter of 76.3 mm. FIG. 3B is an image captured in a position different from the position on the steel pipe P in FIG. 3A in the longitudinal direction. FIG. 3C is a self-luminous image of the steel pipe P with an outer diameter of 101.6 mm whereas FIG. 3D is a self-luminous image of the steel pipe P with an outer diameter of 114.3 mm. As FIGS. 3A to 3D illustrate, although the luminance in the circumferential direction varies depending on the position and the size of the steel pipe P, the luminance in the longitudinal direction is substantially uniform. In the example, as described later, a correction to make more uniform variation in the luminance in the circumferential direction of the self-luminous image is performed using the luminance distribution in the circumferential direction of the self-luminous image.

Figure 4:
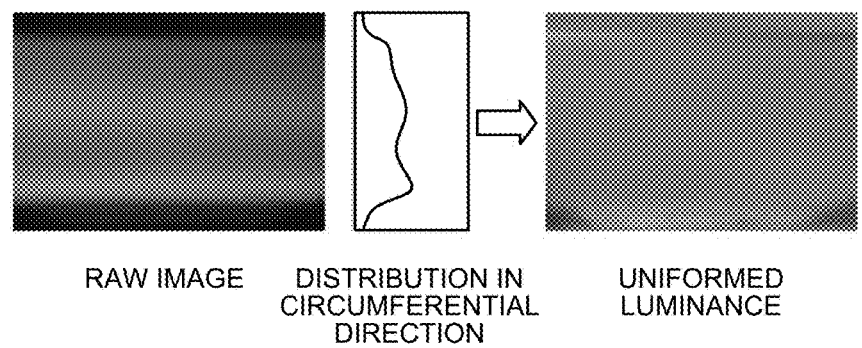
FIG. 4 is an illustrative drawing of making more uniform variation in the luminance in the circumferential direction of the self-luminous image in the example.

At the processing at Step S2, the control device 12 performs processing to make more uniform variation in the luminance in the circumferential direction based on the self-luminous image (a raw image) acquired at the processing at Step S1. Specifically, as FIG. 4 illustrates, the mean value of the luminance in the longitudinal direction is calculated for each of positions in the circumferential direction of the raw image, and the luminance distribution is made using the calculated mean values. The correction to make more uniform the luminance variation in the circumference direction is performed by subtracting the luminance distribution in the circumferential direction from the raw image. When the luminance of the raw material is expressed by formula (1), the luminance distribution in the circumferential direction is expressed by formula (2). The luminance of an image made by subtracting the luminance distribution in the circumferential direction from the raw image is therefore calculated by formula (3).

$$Dr(i, j) \; i = 1 \text{ to } Nx \; j = 1 \text{ to } Ny \tag{1}$$

$$Dy(j) = \frac{1}{Nx}\sum_{i=1}^{Nx} Dr(i, j) \tag{2}$$

$$Dp(i, j) = Dr(i, j) - Dy(j) + 128 \tag{3}$$

The constant in formula (3) (=128) is set to avoid the case that most luminance values acquired by the subtraction are numerically minus. Any number between zero and 255 may thus be set as the constant. The subtraction of formula (3) may be replaced by division.

This process can eliminate the luminance variation caused by disturbance, and an image with uniform luminance is thus obtained. Consequently, it is determined that the luminance variation appearing on the obtained image results from a surface defect. The processing at Step S2 is completed, and the surface inspection processing proceeds to the processing at Step S3.

In the processing, the luminance variation in the circumferential direction is made more uniform by using the fact that the luminance in the longitudinal direction is substantially uniform within the range of a self-luminous image. Considering the entire length of the steel pipe P, however, the luminance in the longitudinal direction of the steel pipe P is not always uniform because the steel pipe P is rotated with rolling and conveyance. The processing to make more uniform the luminance variation in the circumferential direction is sequentially performed on the same self-luminous image or self-luminous images captured in the vicinity thereof.

Figure 5:
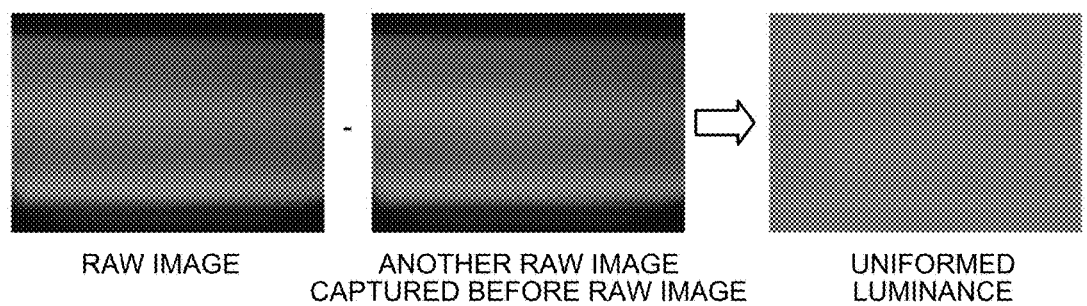
FIG. 5 is an illustrative drawing of making more uniform variation in the luminance in the circumferential direction of a self-luminous image in a different example.

The processing at Step S2 to make more uniform the luminance variation in the circumferential direction may be replaced by the processing illustrated in FIG. 5. Specifically, the luminance variation in the circumferential direction is made more uniform by capturing a plurality of self-luminous images at different positions in the longitudinal direction and calculating a difference in the luminance between any two raw images out of the captured images. More specifically, as illustrated in FIG. 5, an image with the luminance variation in the circumferential direction made more uniform is obtained by extracting the difference between the latest captured raw image and a raw image captured previously by one image. Where formula (4) represents the luminance of a raw image and formula (5) represents another raw image captured previously by one image, formula (6) represents the luminance of an image formed by extracting a difference between both images.

$$Dr(i,j) \; i=1 \text{ to } Nx \; j=1 \text{ to } Ny \tag{4}$$

$$Ds(i,j) \; i=1 \text{ to } Nx \; j=1 \text{ to } Ny \tag{5}$$

$$Dp(i,j)=Dr(i,j)-Ds(i,j)+128 \tag{6}$$

The surface inspection processing can be performed on the entire length of the steel pipe P by changing positions in the longitudinal direction of the steel pipe P and capturing self-luminous images. In this case, it is preferable to use self-luminous images captured at successive timings. Use of images captured in separate timings is not preferable because the luminance variation is different between the images.

At the processing at Step S3, the control device 12 performs processing to detect a surface defect on the steel pipe P using the image with the luminance variation in the circumferential direction made more uniform. The processing at Step S3 is completed, and the flow of the surface inspection processing ends.

As described above, with the manufacturing system 1 for the steel pipe P in this example, the control device 12 makes more uniform the luminance variation in the circumferential direction of a self-luminous image in the range where the luminance is substantially made more uniform in the longitudinal direction. A surface defect on a steel pipe can be therefore detected by using a self-luminous image in a simple device configuration when the steel pipe is hot.

In the example, the thermal image camera 11 captures self-luminous images of the steel pipe P in a position behind the reducer 6, which is because we found that scale attached to the steel pipe P is separated by tensile rolling of the reducer 6. In other words, we found that the number of scale patterns attached to the steel pipe P is reduced with an increase in the diameter reduction rate applied by the reducer 6. The diameter reduction rate is defined by formula (7).

Diameter Reduction Rate=(Outer Diameter of Steel Pipe before Reducer)/Outer Diameter of Steel Pipe after Reducer) (7)

Figure 6A:
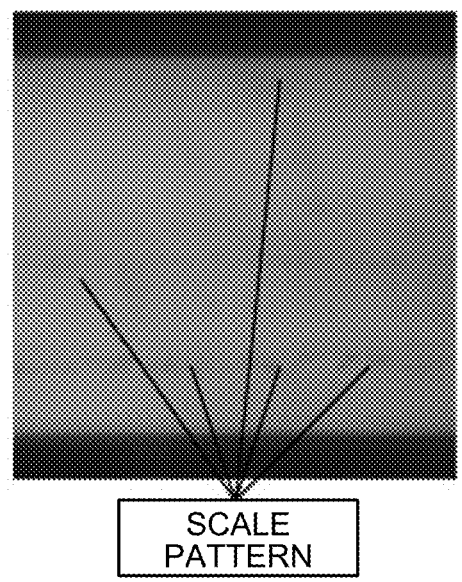
FIG. 6A is an exemplary drawing that illustrates the self-luminous image in the example.
Figure 6B:
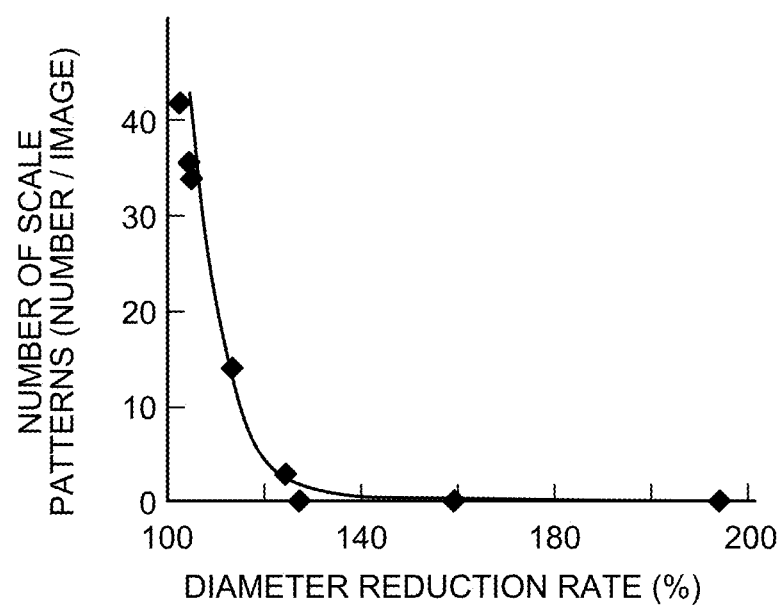
FIG. 6B is an illustrative drawing showing the relationship between a diameter reduction rate and scale in the example.

FIG. 6A is an exemplary drawing that illustrates a self-luminous image captured in a position behind the reducer 6, and a plurality of scale patterns are recognized in FIG. 6A. FIG. 6B is a drawing that illustrates the relationship between the diameter reduction rate applied by the reducer 6 and the number of scale patterns. As FIG. 6B illustrates, an increase in the diameter reduction rate markedly decreases the number of scale patterns. Because the method of rolling by the reducer 6 is tensile rolling, elongation becomes greater as the diameter reduction rate is increased. Detachability of scale attached to the surface is considered to be accordingly increased. Detachability of scale is increased with an increase in the diameter reduction rate. In the viewpoint of more effective scale detachment from the steel pipe P, the diameter reduction rate is preferably at least equal to or greater than 110% and is desirably equal to or greater than 120%. The allowed upper limit of the diameter reduction rate is 500%, which is the upper limit for the equipment.

The place (place to install the thermal image camera 11) to capture a self-luminous image of the steel pipe P is not limited to the place behind the reducer 6. For example, a self-luminous image captured at another place may be usable for a surface inspection of the steel pipe P with less scale.

In the example, a seamless steel pipe is used as an example. The example is similarly applicable for a butt-welded steel pipe made by butting and joining both ends in the width direction when the steel pipe is hot and a welded steel pipe made by tensile rolling after reheating.

An example has been described as above. However, this disclosure is not limited by the description or drawings composing a part of the disclosure based on this example.

Specifically, other constructions, examples, operation techniques and the like made by those skilled in the art based on this example are all included in the scope of the appended claims.

Example

In the manufacturing system of a seamless steel pipe, a CMOS camera sensitive to the near infrared region was disposed behind a reducer. A filter that blocks visible light was installed on all the surfaces of the thermal image camera, and images were captured in the near infrared region having a wavelength of equal to or longer than 700 nm. A longer wavelength may be used such as a wavelength of equal to or shorter than 20 μm in the infrared region. In the example, the interval between timings for capturing images was determined based on the conveyance speed of the steel pipe to not have any self-luminous images omitted. Images were captured at around every 100 mm to 500 mm position in the longitudinal direction of the steel pipe with resolution in a pitch of 1 mm. The temperature of the material was 600° C. to 1000° C.

Figure 7:
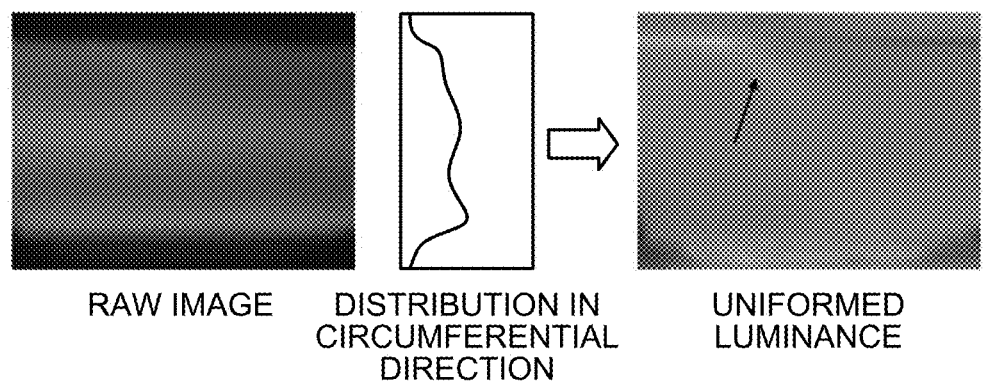
FIG. 7 is a drawing that illustrates a surface inspection result in the example.
Figure 8:
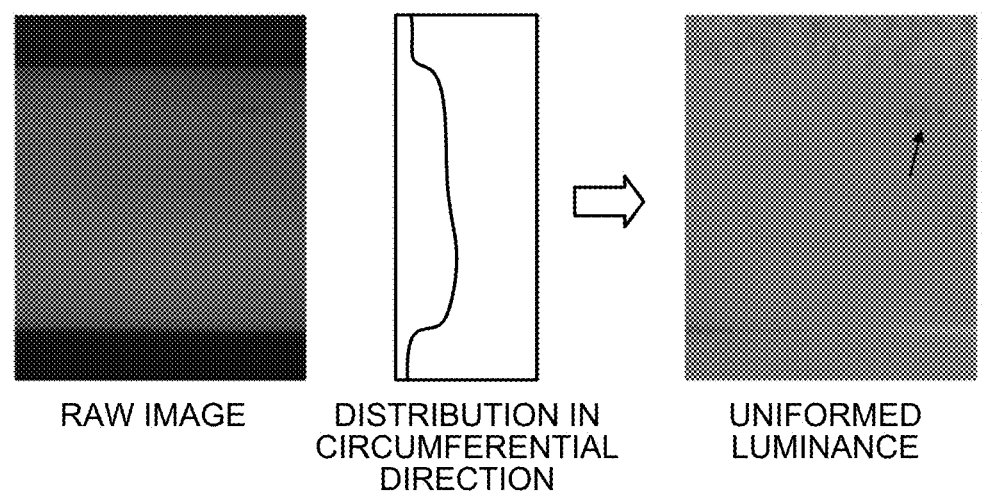
FIG. 8 is another drawing that illustrates a surface inspection result in the example.

FIGS. 7 and 8 illustrate examples of detecting a surface defect on a seamless steel pipe. The diameter reduction rate in FIGS. 7 and 8 are, respectively, 160% and 125%. On each self-luminous image, scale patterns are reduced. After a correction to make more uniform the luminance variation in the circumference direction, images free from effects of disturbance and having made more uniform luminance were obtained. As indicated by arrows in FIGS. 7 and 8, defects in the bright and dark sides were clearly detected in the respective drawings. After cooling the steel pipe, investigation on these positions was carried out. With the investigation, a lap defect resulting from a rolling defect and a biting defect with a dent on the surface were found. In this manner, surface defects on a steel pipe can be detected when the steel pipe is hot in a simple device configuration.

Figure 9:
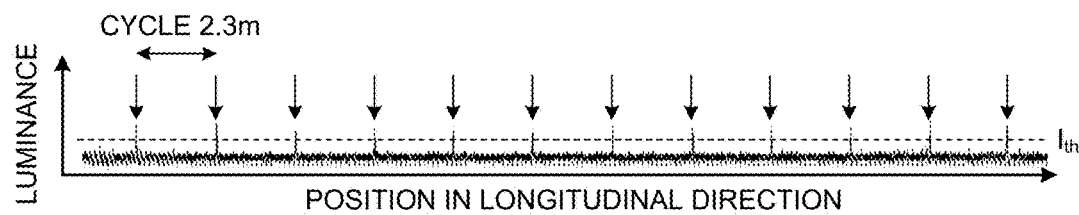
FIG. 9 is a chart that illustrates a luminance distribution in the longitudinal direction of the steel pipe.
Figure 10:
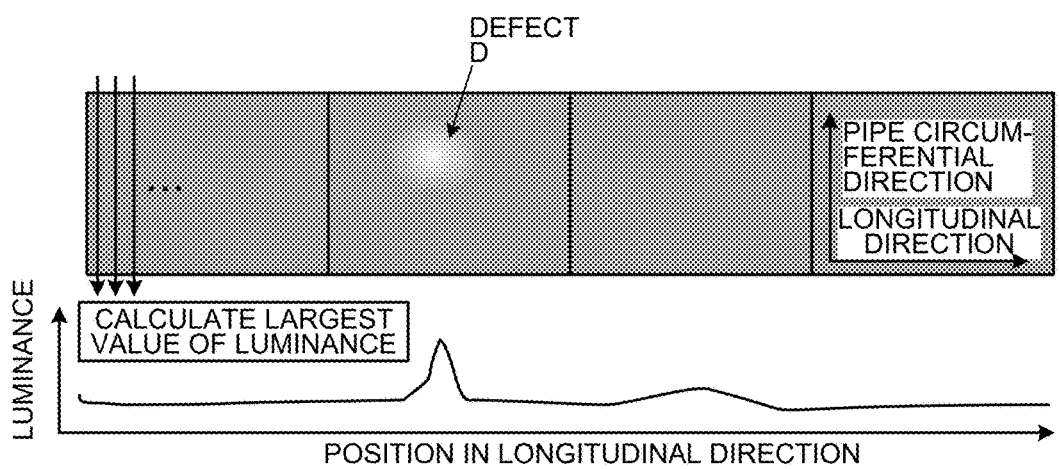
FIG. 10 is an illustrative drawing for a method of calculating the luminance distribution illustrated in FIG. 9.

A method of manufacturing a steel pipe will be described with reference to FIGS. 9 and 10. FIG. 9 is a chart to calculate the luminance distribution in the longitudinal direction of the steel pipe based on intermittently extracted images in the longitudinal direction of the steel pipe in a manner synchronized with the steel pipe conveyance and having no images omitted. In the example, as illustrated in FIG. 10, the largest luminance value in the pipe circumferential direction was calculated at each position in the longitudinal direction (the pipe axis direction), whereby the luminance distribution in the longitudinal direction was calculated. In this manner, the chart illustrated in FIG. 9 was worked out. Based on the chart, the luminance was compared to a threshold, thereby detecting a surface defect.

A surface defect detected position in the longitudinal direction of the steel pipe can be calculated based on the pitch in which the image was extracted and the position of the surface defect in the longitudinal direction in the luminance distribution. In this manner, it is possible to find the surface defect detected position in the longitudinal direction of the steel pipe. When a plurality of surface defects have been detected, it is thus possible to determine whether regularity is seen in the surface defect detected positions based on the respective positions in the longitudinal direction. If regularity is seen in the surface defect detected positions, the cycle (the consecutive distance appearing in the longitudinal direction, in the example of FIG. 9, the cycle is 2.3 m) can be determined.

The surface defects having regularity in the detected positions result from a rolling mill roll and a conveyance roll. In other words, a roll having the diameter corresponding to the cycle is a cause of the surface defects. The diameter of the roll differs from the diameters of the piercer 3, the mandrel mill 4, the reducer 6, and a conveyance roll (not illustrated) in FIG. 1. The cause of the surface defects can be thus determined while considering stretch of the steel pipe by the rolling.

On the other hand, if no regularity is seen in the surface defect detected positions, it can be determined that the defect has been caused not by rolls but by inclusions entering the surface portion in the steel making stage. More specifically, the surface defect without regularity in the detected position is a defect existing in a depth of about 0.1 to 2 mm from the surface. Such a defect results from a blowhole, mold powder involved during continuous casting, and oxide folded on the surface during rolling, which happened to be included on the lap.

In this manner, the cause of a surface defect can be identified. In surface defects having regularity in the detected positions, the manufacturing conditions in the steel pipe manufacturing process are changed. Specifically, the surface defect can be prevented by inspecting the surface of a roll determined to be a cause of the defect and replacing the abnormal roll. In a surface defect without regularity in the detected position, the operation conditions in the steel making stage are changed. Specifically, factors are examined such as the casting speed, the kind of powder to be used, the tolerance to a fluctuation in the molten metal surface level, a set value for the in-mold electro-magnetic stirring, and the shape of a submerged nozzle.

As described above, with the surface defect inspection device for a steel pipe, the cause of a surface defect can be identified immediately after rolling, thereby manufacturing a steel pipe with high surface quality without producing a large number of non-conforming products.

An example has been described as above. However, this disclosure is not limited by the description based on this example. Other constructions, examples, operation techniques and the like made by those skilled in the art based on this example are all included in the scope of the appended claims.

INDUSTRIAL APPLICABILITY

A surface inspection method, a surface inspection device, a manufacturing system, a method of identifying a defect formed area, and a manufacturing method of a steel pipe, which aim to detect a surface defect on the hot steel pipe using a self-luminous image, are provided.

The invention claimed is:

1. A surface inspection method for inspecting a steel pipe emitting light as a result of hot rolling, the method comprising:
   imaging a self-luminous image of a surface of the steel pipe in longitudinal direction and circumferential direction after the hot rolling, luminance of the self-luminous image depending on a surface temperature of the steel pipe;
   correcting the luminance of the self-luminous image by making variation in the luminance more uniform in a circumferential direction of the self-luminous image; and
   detecting a surface defect based on the self-luminous image whose luminance has been corrected.

2. The method according to claim 1, wherein the self-luminous image is captured in a position behind a reducer.

3. The method according to claim 2, wherein a diameter reduction rate applied by the reducer for the steel pipe is equal to or greater than 110%.

4. The method according to claim 1, wherein the correcting step makes more uniform luminance variation in the circumferential direction of the self-luminous image by using a luminance distribution in the circumferential direction where luminance in a longitudinal direction of the steel pipe on the self-luminous image is averaged.

5. The method according to claim 1, wherein the correcting step makes more uniform a luminance variation in the circumferential direction of the self-luminous image by using a difference in luminance between a plurality of self-luminous images captured with a position in a longitudinal direction of the steel pipe changed.

6. The method according to claim 1, wherein the imaging step captures the self-luminous image by using a bandwidth of equal to or longer than 700 nm wavelength of near infrared light and equal to or shorter than 20 μm wavelength of infrared light.

7. A method of identifying a defect formed area on a steel pipe, the method comprising:
inspecting the steel pipe and detecting a surface defect on the steel pipe with the method according to claim 1;
determining that the surface defect is caused in a steel pipe manufacturing process when regularity is seen in a position where the surface defect has been detected; and
determining that the surface defect is caused at a steel making stage when irregularity is seen in the position where the surface defect has been detected.

8. A method of manufacturing a steel pipe, comprising:
changing a manufacturing condition in a steel pipe manufacturing process and/or an operation condition at a steel making stage to prevent generation of a further surface defect based on a cause of the surface defect identified with the method of identifying a defect formed area according to claim 7.

9. A surface inspection device for inspecting a steel pipe emitting light as a result of heating, the device comprising:
an imaging device configured to capture a self-luminous image of a surface of the steel pipe, luminance of the self-luminous image depending on a surface temperature of the steel pipe;
a correcting device configured to correct the luminance of the self-luminous image by making variation in the luminance more uniform in a circumferential direction of the self-luminous image; and
a detecting device configured to detect a surface defect based on the self-luminous image whose luminance has been corrected.

10. A steel pipe manufacturing system comprising the device according to claim 9.

* * * * *